(12) United States Patent
Harris et al.

(10) Patent No.: US 8,202,712 B2
(45) Date of Patent: Jun. 19, 2012

(54) TRIGLYCERIDE PROCESS

(75) Inventors: John Bernard Harris, Wormerveer (NL); Ulrike Schmid, Wormerveer (NL); Frederick William Cain, Voorburg (NL)

(73) Assignee: Loders Croklaan B.V., Wormerveer (NL)

( * ) Notice: Subject to any disclaimer, the term of this patent is extended or adjusted under 35 U.S.C. 154(b) by 890 days.

(21) Appl. No.: 11/991,612

(22) PCT Filed: Sep. 8, 2006

(86) PCT No.: PCT/GB2006/003345
§ 371 (c)(1),
(2), (4) Date: Oct. 6, 2008

(87) PCT Pub. No.: WO2007/029020
PCT Pub. Date: Mar. 15, 2007

(65) Prior Publication Data
US 2009/0123982 A1    May 14, 2009

(30) Foreign Application Priority Data

Sep. 8, 2005 (EP) .................................. 05255491

(51) Int. Cl.
*C12P 7/64* (2006.01)
*C11C 1/00* (2006.01)
*C09K 3/00* (2006.01)
*C11C 3/00* (2006.01)

(52) U.S. Cl. .................... 435/134; 435/271; 252/182.1; 554/121; 554/163

(58) Field of Classification Search ................. 435/134, 435/271; 554/163, 121; 252/182.12
See application file for complete search history.

(56) References Cited

U.S. PATENT DOCUMENTS

| | | | |
|---|---|---|---|
| 4,268,527 A | 5/1981 | Matsuo et al. | 426/33 |
| 4,876,107 A | 10/1989 | King et al. | 426/601 |
| 5,288,619 A | 2/1994 | Brown et al. | 435/134 |
| 6,090,598 A | 7/2000 | Yamaguchi et al. | 435/134 |

FOREIGN PATENT DOCUMENTS

| | | |
|---|---|---|
| EP | 0209327 | 1/1987 |
| EP | 0245076 | 11/1987 |
| EP | 0 882 797 A2 | 12/1998 |
| EP | 1 477 070 A1 | 11/2004 |
| GB | 1577933 | 10/1980 |
| WO | WO 2005/014575 | 2/2005 |

OTHER PUBLICATIONS

Chen et al., "Synthesis of the structured lipid 1,3-Dioleoyl-2-palmitoylglycerol from palm oil", Journal of the American Oil Chemists' Society, 91(6):525-532 (2004).
Filer et al., "Triglyceride Configuration and Fat Absorption by the Human Infant" J. Nutrition, 99:293-298, Nov. 1969.
Freeman et al., "Intramolecular fatty acid distribution in the milk fat triglycerides of several species" J. Dairy Sci., 48:853-858 (1965).
Goto et al., "Enzymatic Interesterification of Triglyceride with Surfactant-Coated Lipase in Organic Media", Biotechnology and Bioengineering, 45(1):27-32 (1995).
Nakaya et al., Transesterification between triolein and stearic acid catalyzed by lipase in CO2 at various pressures, Biotechnology Techniques, 12(12):881-884 (1998).
Seriburi et al., "Enzymatic transesterification of Triolein and Stearic acid and solid fat content of their products", Journal of the American Oil Chemists' Society, 75(4):511-516 (1998).
Soumanou et al., "Two-step Enzymatic Reaction for the Synthesis of Pure Structured Triacylglycerides", Journal of the American Oil Chemists' Society, 75(6):703-710 (1998).
Soumanou et al., "Synthesis of structured triglycerides by lipase catalysis", Fett-Lipid, 100(4-5):156-160 (1998).

*Primary Examiner* — Herbert J Lilling
(74) *Attorney, Agent, or Firm* — Morgan, Lewis & Bockius LLP

(57) ABSTRACT

A process for producing triglycerides which comprises: (a) subjecting a first triglyceride comprising at least 40% by moles of oleic acid residues, based on total acyl groups in the triglyceride, to an alcoholysis reaction with an alcohol having from 1 to 6 carbon atoms to obtain a composition comprising 2-oleoyl monoglyceride and at least one acyl ester of said alcohol; (b) reacting the 2-oleoyl monoglyceride with an acylating agent comprising at least one C12 to C24 saturated fatty acid, at least one ester of said fatty acid or a mixture thereof, to obtain a 1,3-saturated fatty acid acyl 2-oleoyl glyceride; and (c) separating at least a part of the at least one acyl ester after or during step (a) or step (b); (d) reacting the acyl ester with a second glyceride to form 1,3-dioleoyl 2-palmitoyl glyceride.

12 Claims, No Drawings

TRIGLYCERIDE PROCESS

This invention relates to a process. In particular, the invention relates to a process for producing triglycerides, in particular 1,3-dioleoyl-2-palmitoyl glyceride (OPO) and a 1,3-saturated fatty acid acyl 2-oleoyl glyceride.

Triglycerides are important components of many products, especially food products. The triglyceride 1,3-dioleoyl-2-palmitoyl glyceride is an important glyceride component of human milk fat.

Fat compositions containing similar amounts of the principal fatty acids found in human milk fat may be derived from oils and fats of vegetable origin. However, there remains a significant difference in composition between milk replacement fats, derived from natural sources, and that of human milk fat. This difference arises because most glycerides of vegetable origin are unsaturated in the 2-position. In contrast, a substantial amount of palmitic acid occupies the 2-position of glycerides in human milk fat.

The difference in the distribution of acids along the glyceride positions is believed to have important dietary consequences. The distribution of fatty acids in the triglycerides of some milk fats of nutritional importance was studied by Freeman et al, (*J. Dairy Sci.*, 1965, p. 853), who reported that human milk fat contains a greater proportion of palmitic acid in the 2-position, and a greater proportion of stearic acid and oleic acid in the 1,3-positions than the milk fit of ruminants. The greater absorption of palmitic acid in the 2-position of triglycerides by infants was reported by Filer et al (*J. Nutrition*, 99, pp. 293-298), who suggest that the relatively poor absorption of butter fat by infants compared with human milk fat is attributable to its substantially uniform distribution of palmitic acid between the glyceride positions of the fat.

In order to most closely match the chemical and/or physical properties of triglyceride fats or oils obtained from natural sources, to that of human milk fat, therefore, it is necessary to control the distribution of the fatty acid residues on the glyceride positions.

EP-A-0209327 discloses milk replacement fat compositions comprising the triglyceride 1,3-dioleoyl-2-palmitoyl glyceride. According to EP-A-0209327, these fat compositions can be obtained by subjecting fatty mixtures comprising glycerides consisting substantially of more saturated 2-palmitoyl glycerides to a rearrangement catalyst, such as a lipase, which is regiospecific in activity in the 1- and 3-positions of the glycerides. Enzymatic processes of this kind are also described in GB 1577933. Under the influence of the catalyst, unsaturated fatty acid residues may be introduced into the 1- and 3-positions of the 2-palmitoyl glycerides by exchange with unsaturated free fatty acids or their alkyl esters.

U.S. Pat. No. 6,090,598 discloses an enzymatic process for interesterification of fats and oils using distillation.

There remains a need to provide a more efficient process for the production of 1,3-dioleoyl-2-palmitoyl glyceride (OPO).

The present invention provides, in one aspect, a process for producing triglycerides which comprises:
  (a) subjecting a first triglyceride comprising at least 40% by moles of oleic acid residues, based on total acyl groups in the triglyceride, to an alcoholysis reaction with an alcohol having from 1 to 6 carbon atoms to obtain a composition comprising 2-oleoyl monoglyceride and at least one acyl ester of said alcohol;
  (b) reacting the 2-oleoyl monoglyceride with an acylating agent comprising at least one C12 to C24 saturated fatty acid, at least one ester of said fatty acid or a mixture thereof to obtain a 1,3-saturated fatty acid acyl 2-oleoyl glyceride;
  (c) separating at least a part of the at least one acyl ester after or during step (a) or step (b); and
  (d) reacting the acyl ester with a second glyceride to form 1,3-dioleoyl 2-palmitoyl glyceride.

In another aspect, the invention provides the use of a triglyceride comprising at least 40% by moles of oleic acid residues, based on total acyl groups in the triglyceride, in a process for producing both 1,3-saturated fatty acid acyl 2-oleoyl glyceride and 1,3-dioleoyl 2-palmitoyl glyceride.

Also provided by the invention in a further aspect is the use of 2-oleoyl monoglyceride for producing a 1,3-saturated fatty acid acyl 2-oleoyl glyceride, wherein the 2-oleoyl monoglyceride is formed by the alcoholysis of a triglyceride.

Further provided by the invention in yet another aspect is the use of an acyl ester for producing 1,3-dioleoyl 2-palmitoyl glyceride, wherein the acyl ester is formed by the alcoholysis of a triglyceride.

The process of the invention is an efficient process for the production of OPO glyceride. Surprisingly, a process for the production of OPO has been discovered which produces a by-product that is useful in the manufacture of other triglycerides.

The term "stearin" as used in this specification, includes a triglyceride mixture or fat blend from which at least 10% by weight of the lower melting constituents have been removed by some kind of fractionation, e.g., dry fractionation, Lanza fractionation or solvent fractionation.

The term fatty acid, fatty acyl groups, and related terms used herein refer to saturated or unsaturated, straight chain carboxylic acids having from 4 to 24 carbon atoms, preferably from 12 to 22 carbon atoms. Unsaturated acids may comprise one, two, or more double bonds, preferably one or two double bonds.

The term alkyl, as used herein, refers to straight chain or branched saturated hydrocarbons having from 1 to 6 carbon atoms.

The first triglyceride used in step (a) of the present invention is preferably high oleic sunflower oil (HOSF) or a fraction thereof. Fractions include products obtained from HOSF by fractionation, such as solvent or dry fractionation, which alters the composition of the product. The high oleic sunflower oil or fraction thereof has at least 40%, preferably at least 50%, such as 60%, and most preferably at least 70% by moles of oleic acid residues, based on total acyl groups in the triglyceride. High oleic sunflower oil is typically obtained from the oil contained in the seeds of sunflowers.

Before the first triglyceride is reacted with the alcohol in step (a) of the process of the invention, the first triglyceride is optionally degummed and/or refined, using standard techniques known in the art.

Steps (a) and/or (d) in the process of the present invention are preferably carried out in the presence of an enzyme, more preferably a lipase.

Step (a) is typically carried out in the presence of a 1,3 specific lipase as a biocatalyst. During step (a), the fatty acids on the 2-position of the first glyceride typically do not change (for example, less than 10% by number (or moles) of fatty acyl groups in the 2-position, more preferably less than 5%, such as less than 1%) change during the process.

Under the influence of a 1,3 specific lipase in step (a) of the process (i.e., in the alcoholysis reaction), the fatty acyl groups in the 1- and 3-positions are hydrolysed to the corresponding hydroxyl groups. Therefore, the 1,3 specific lipase selectively hydrolyses the acyl groups on the 1- and 3-positions rather than the 2-position.

The alcoholysis reaction may be carried out using standard techniques known in the art. Preferably the reaction is carried out in the presence of a solvent, preferably an organic solvent, e.g., a $C_3$ to $C_{10}$ ketone, such as acetone.

Alcohols used in the alcoholysis reaction according to the process of the present invention may be straight chain or branched alcohols having from 1 to 6 carbon atoms, for example, methanol, ethanol and propan-1-ol. Alcohols may be single compounds or mixtures of two or more different compounds. Preferably, the alcohol is ethanol.

The acyl ester obtained in step (a) of the process of the present invention is preferably ethyl oleate.

The composition obtained in step (a) preferably comprises at least 60%, more preferably at least 70%, such as at least 80%, most preferably at least 90% 2-oleoyl monoglyceride by weight, based on the triglycerides in the composition.

After step (a) of the process, at least a portion of the alcohol and/or any solvent is preferably removed using, for example, reduced pressure. The separation may be carried out using vacuum distillation at temperatures below 65° C., more preferably below 60° C., such as below 55° C., most preferably below 50° C., for example from 20° C. to 50° C.

The acyl ester is separated from the reaction mixture after or during step (a) or step (b), preferably after step (a) or after step (b). Separation of the acyl ester from the 2-monoglyceride after step (a) and separation of the acyl ester from the triglyceride after step (b) may be achieved by any known techniques in the art, for example, by fractional distillation.

Preferably, a mixture of the acyl ester and the 2-oleoyl monoglyceride is reacted in step (b) and separation of the acyl ester takes place after step (b).

The composition comprising 2-oleoyl monoglyceride, obtained after step (a), optionally after removal of a portion of the acyl ester, is reacted with an acylating agent. The acylating agent may comprise one or more saturated fatty acids such as stearic acid, palmitic acid, myristic acid, lauric acid and mixtures thereof. Alternatively or additionally, the acylating agent may comprise one or more esters of the saturated fatty acids; preferred esters are $C_1$ to $C_6$ alkyl esters and triglycerides (including mono, di and tri glycerides). Acids and esters may be used singly or as mixtures and one or more acids may be used together with one or more esters. Preferably, the acylating agent comprises stearic acid. The acylating agent is typically present in excess based on the 2-oleoyl glyceride, for example from 1.1 molar to 10 molar excess.

Step (b) is preferably carried out in the presence of an enzyme, preferably a 1,3 specific lipase. During the acylation reaction of step (b), the fatty acids on the 2-position of the 2-oleoyl monoglyceride typically do not change (for example, less than 10% by number (or mole) of fatty acyl groups in the 2-position, more preferably less than 5%, such as less than 1%) change during the process.

Under the influence of the 1,3 lipase during the acylation reaction, saturated fatty acid residues may be introduced into the 1- and 3-positions of the monoglyceride.

The 1,3-saturated fatty acid acyl 2-oleoyl glyceride obtained in step (b) of the process of the present invention is preferably separated from the reaction mixture by, for example, fractionally distilling off any acyl ester and excess acylating agent. Water is also typically removed to produce a composition comprising more than 50%, preferably more than 60%, such as more than 70%, most preferably more than 75% by weight 1,3-saturated fatty acid acyl ester 2-oleoyl glyceride.

The preferred 1,3-saturated fatty acid-acyl 2-oleoyl glyceride produced in step (b) in the process of the present invention is 1,3-distearoyl 2-oleoyl glyceride. 1,3-Distearoyl 2-oleoyl glyceride (also known as StOSt) is a valuable commercial product. For example, it may be used, either alone or together with other glycerides such as 1,3-dipalmitoyl 2-oleoyl glyceride, as a cocoa butter equivalent or substitute.

The triglyceride used as the other starting material in step (d) of the process of the present invention preferably comprises at least 50%, preferably at least 60%, most preferably at least 70% by moles of palmitic acid residues, based on total acyl groups. Preferably, the triglyceride used in step (d) comprises glycerides which contain palmitic acid in the 2-position of the glycerol backbone, which may be obtained from the high melting fraction of palm oil. Palm oil contains up to 12% by weight trisaturated acid glycerides including tripalmitin. Generally, a top fraction contains 4 parts tripalmitin and 1 part of symmetrical disaturated triglycerides, by weight. The high melting fraction of palm oil is preferably fractionated to obtain palm oil stearin preferably comprising saturated 2-palmitoyl glycerides, typically in an amount of greater than 60% by weight, such as greater than 70% by weight or greater than 75% by weight. Fractionation of palm oil may be carried out by solvent (wet) fractionation, Lanza fractionation, or dry fractionation, such as multi-stage countercurrent dry fractionation, of palm oil. The palm oil can be crude palm oil, refined palm oil, fractions of palm oil or mixtures thereof. Preferably, the palm oil is subjected to wet fractionation using an organic solvent (e.g., a $C_3$ to $C_{10}$ ketone, such as acetone) or an aqueous medium comprising surfactants. Palm oil stearin is typically refined, which preferably involves bleaching and deodorizing. The bleaching of the palm oil is preferably performed at high temperatures, preferably above 100° C., such as 110° C. In the deodorizing step, volatile impurities are removed from the palm oil stearin at temperatures above 200° C. to yield deodorized palm oil stearin. The impurities removed in the deodorizing step commonly include free fatty acids, aldehydes, ketones, alcohols and other hydrocarbon impurities. The bleaching and deodorizing are performed under standard conditions known in the art and may be carried out in a single process step or two or more process steps. For example, the steps may be carried out at reduced pressures (e.g., 10 mm Hg or below), wherein the palm oil stearin is contacted with steam to help vaporize the impurities or, alternatively, the deodorizing step may be carried out at elevated temperature and a pressure of no greater than, for example, 10 mm Hg.

Step (d) in the process of the present invention is preferably carried out in the presence of an enzyme, preferably a 1,3 specific lipase. During the reaction of the second glyceride with the acyl ester, the fatty acids on the 2-position of the second glyceride typically do not change (for example, less than 10% by number (or moles) of fatty acyl groups in the 2-position, more preferably less than 5%, such as less than 1%) change during the process.

Under the influence of the 1,3 lipase during step (d), oleoyl residues from the acyl ester are introduced into the 1- and 3-positions of the triglyceride by exchange with the fatty acid residues of the triglyceride. The 2-palmitoyl glycerides modified in this way may be separated from the reaction mixture.

The reaction in step (d) in the process of the present invention selectively exchanges palmitic acid with oleic acid on the 1,3-position rather than the 2-position. The reaction is performed to reach or approach equilibrium at a conversion ratio to 1,3-dioleoyl 2-palmitoyl glyceride of a minimum of 50%, preferably at least 60%, most preferably at least 70% by moles based on the second glyceride.

Preferably, in step (d), palm oil stearin as triglyceride is, for example, mixed with the acyl ester (comprising ethyl oleate at a concentration of greater than 65% by weight, preferably greater than 70% by weight, most preferably greater than 75% by weight). The ratio of palm oil stearin to ethyl oleate is preferably from 0.1:1 to 2:1, more preferably from 0.4:1 to 1.2:1, even more preferably from 0.4:1 to 1:1, most preferably from 1:1.1 to 1:2 on a weight basis. The reaction is preferably carried out at a temperature from 30° C. to 90° C., preferably from 50° C. to 80° C., such as around 60° C. to 70° C., and may be conducted batchwise or in continuous fashion, with or without a water-immiscible organic solvent.

Before the reaction of step (d), the humidity is preferably controlled to a water activity between 0.05 and 0.55, preferably between 0.1 and 0.5, depending on the type of biocatalyst enzyme system used. The reaction may be performed, for example, at 60° C. in a stirred tank or in a packed bed reactor over biocatalysts, based on concentrates of Lipase D (*Rhizopus oryzae*, previously classified as *Rhizopus delemar*, from Amano Enzyme Inc., Japan) or immobilised concentrates of *Rhizomucor miehei* (Lipozyme RM IM from Novozymes, Denmark).

The 1,3-dioleoyl 2-palmitoyl glyceride obtained in step (d) is preferably subjected to a further step in which it is purified. In order to separate the fatty acids and esters from the product triglyceride fraction, the composition obtained in step (d) (optionally after further treatment, such as isolation of the fat phase) may be distilled at low pressure (<10 mbar) and elevated temperatures (>200° C.).

After distillation of the 1,3-dioleoyl 2-palmitoyl glyceride obtained in step (d), the triglyceride fraction is preferably fractionated to recover the OPO glyceride. This can be done using solvent fractionation or dry fractionation, using a single, two-step or multi-step fractionation technique, but is preferably carried out using single step dry fractionation. Fractionation preferably removes the unconverted tri-palmitins down to a level of less than 15 weight %, preferably less than 10 weight %, most preferably less than 6 weight %. The OPO fraction is typically fully refined to remove all remaining fatty acids and contaminants to produce a refined OPO fraction.

The invention may comprise one or more additional steps of further purifying the 1,3-dioleoyl 2-palmitoyl glyceride.

The process may optionally comprise further steps before, between or after (a) to (d), such as partial purification or enrichment of the products in the desired component(s).

The composition comprising OPO glycerides that is produced by the process of the present invention may comprise OPO glycerides preferably in an amount of at least 50% by weight, more preferably at least 60% by weight. The balance comprises other non-OPO triglycerides. The composition comprises a mixture of triglycerides wherein different fatty acid residues, including unsaturated fatty acid residues, are randomly distributed between the 1- and 3-positions and at least half of the fatty acid residues in the 2-positions are C16 and/or C18 saturated, preferably consisting substantially of palmitic acid residues, in particular 60-90% by weight of the total 2-position fatty acids. Preferably all of the fatty acid residues, or virtually all (e.g., greater than 99% by weight), are even-numbered. The unsaturated fatty acid residues in the 1- and 3-positions preferably consist largely of oleic acid, linoleic acid and palmitic acid. The composition preferably includes at least as much (on a molar basis) of saturated fatty acid in the 2-position as in the 1- and 3-positions combined, more preferably up to twice as much (on a molar basis). Preferably, the 1,3-positions include both unsaturated C18 and saturated C4 to C14 fatty acids. The proportion and type of these fatty acids may be determined in accordance with dietary and physical requirements of the composition required. For example, milk replacement fats should be capable of emulsification at blood heat in liquid feed and should therefore preferably be capable of being melted at this temperature (37° C.). The melting point of fats is determined by their fatty acid composition, which may be selected accordingly. Fats with the correct fatty acid composition may be selected for use in the present invention, therefore, with a view to producing fat compositions with certain desired physical characteristics.

The most preferred compositions produced by the present invention are those comprising OPO glycerides comprising at least 50 wt % palmitic acid present in the 2-position, less than 8 wt % SSS wherein S represents saturated fatty acid having at least 18 carbon atoms, preferably 18 carbon atoms, and at least 40 wt % oleic acid residues in the 1 and 3 positions.

The composition obtained by the process of the present invention contains preferably less than 10% by weight 1,2,3-trisaturated glycerides, preferably less than 8% by weight 1,2,3-trisaturated glycerides.

The process of the present invention may comprise the further step of blending the OPO fraction with other fats and/or oils, preferably at least one vegetable oil, to form fat blends. Suitable fats are fats comprising up to 40 wt % of medium-chain triglycerides; up to 30 wt % of lauric fats; up to 50 wt % of other vegetable fats; or up to 40 wt % of butterfat; or fractions or mixtures of these fats. In particular, lauric fats, preferably palm kernel oil, may be included in the compositions to provide blends matching the compositions of milk fat or its melting characteristics, and/or vegetable oils such as sunflower oil, high oleic sunflower oil, palm kernel oil, rapeseed oil, high oleic safflower oil, coconut oil and soybean oil, which have a high content of polyunsaturated fatty acid glycerides, which improve the dietary benefit of the compositions, may be included. In this way, the compositions produced by the process of the invention preferably provide blends matching the composition of milk fat or its melting characteristics. The best compositions are obtained when the Solid Content Index measured by NMR-pulse on non stabilised fats are within the following ranges: N0=35–55; N10=25–50 and N30</=10. These values were obtained by melting the fat at 80° C., holding the fat at 60° C. or higher for at least 10 minutes, cooling to 0° C. and holding the fat at 0° C. for 16 hours, heating the fat to the measurement temperature N and holding the fat at that temperature for 30 minutes before measuring the N value.

The fat compositions or fat blends produced by the process of the invention are suitable for replacing at least a part of the fat in infant food formulations. The present invention also therefore provides for a method for the production of infant food compositions comprising fat, protein and carbohydrate components in the approximate relative weight proportions 2.5:1:5, wherein at least a part of the fat normally used in such formulations is replaced by the fat composition or fat blend made in accordance with the present invention. Dry formulations containing this mixture, together with additional components customary in sum formulations, should be dispersed for use in sufficient water to produce an emulsion of approximately 3½ grams of fat per 100 ml of dispersion.

The following non-limiting example illustrates the invention and does not limit its scope in any way. In the examples and throughout this specification, all percentages, parts and ratios are by weight unless indicated otherwise.

Example

Triolein is dissolved in acetone and equilibrated to a defined water activity of 0.43. Dry ethanol is added and the mixture stirred at 52° C. Then the reaction is started by addition of 2% (based on the weight of triolein) of an immobilised 1,3 specific lipase such as RML (lipase form *Rhizomocur miehei*) or RDL (lipase from *Rhizopus delemar*). The reaction is stopped when the conversion is about 90% to 2-monoglycerides (approximately 48 h) by removal of the immobilized lipase. After removal of excess acetone and ethanol at temperatures below 50° C. in a vacuum distillation, the residue consisting of 2-monoolein and ethyl oleate is reacted with stearic acid in the presence of 2% by weight (based on the weight of 2-monoglyceride) of a 1,3 specific enzyme at 60° C. to form 1,3-distearoyl-2-oleyl glyceride (first product). The water activity should be 0.11. The water formed during the esterification process is removed by vacuum. Ethyl oleate and the excess of stearic acid are removed by fractional distillation. The recovered ethyl oleate is subjected to an enzymatic reaction with tripalmitin and a 1,3-specific lipase to form 1,3-dioleoyl-2-palmitoyl glyceride (second product). The lipase is RML or RDL.

The invention claimed is:

1. A process for producing triglycerides which comprises:
   (a) subjecting a first triglyceride comprising at least 40% by moles of oleic acid residues, based on total acyl groups in the triglyceride, to an alcoholysis reaction with an alcohol having from 1 to 6 carbon atoms to obtain a composition comprising 2-oleoyl monoglyceride and at least one acyl ester of said alcohol;
   (b) reacting the 2-oleoyl monoglyceride with an acylating agent comprising at least one C12 to C24 saturated fatty acid, at least one ester of said fatty acid or a mixture thereof, to obtain a 1,3-saturated fatty acid acyl 2-oleoyl glyceride;
   (c) separating at least a part of the at least one acyl ester after or during step (a) or step (b); and
   (d) reacting the acyl ester with a second glyceride to form 1,3-dioleoyl 2-palmitoyl glyceride.

2. Process as claimed in claim 1, wherein (a) and/or (c) and/or (d) is or are carried out in the presence of an enzyme as catalyst.

3. Process as claimed in claim 2, wherein the enzyme is a lipase.

4. Process as claimed in claim 3, wherein the alcohol is ethanol.

5. Process as claimed in claim 4, wherein the acyl ester comprises ethyl oleate.

6. Process as claimed in claim 1, wherein (a) is carried out in the presence of a solvent.

7. Process as claimed in claim 6, wherein after (a) at least a portion of the alcohol is removed from the composition.

8. Process as claimed in claim 7, wherein the 1,3-saturated fatty acid acyl 2-oleoyl glyceride obtained in (b) is purified.

9. Process as claimed in claim 1, wherein the second glyceride comprises at least 50% by moles of palmitic acid residues, based on total acyl groups.

10. Process as claimed in claim 1, wherein the 1,3-dioleoyl 2-palmitoyl glyceride obtained in (d) is purified.

11. Process as claimed in claim 1, wherein the 1,3-saturated fatty acid acyl 2-oleoyl glyceride obtained in (b) is 1,3-distearoyl 2-oleoyl glyceride.

12. Process as claimed in claim 1, wherein the first triglyceride is high oleic sunflower oil (HOSF) or a fraction thereof.

* * * * *